(12) United States Patent
Cheng et al.

(10) Patent No.: US 12,220,191 B2
(45) Date of Patent: Feb. 11, 2025

(54) MECHANICAL ARM AND CONTROL METHOD THEREFOR

(71) Applicant: AGIBOT MEDTECH (SUZHOU) CO., LTD., Jiangsu (CN)

(72) Inventors: Hao Cheng, Jiangsu (CN); Min Xu, Jiangsu (CN)

(73) Assignee: AGIBOT MEDTECH (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 18/283,181

(22) PCT Filed: Apr. 7, 2022

(86) PCT No.: PCT/CN2022/085605
§ 371 (c)(1),
(2) Date: Sep. 20, 2023

(87) PCT Pub. No.: WO2022/247481
PCT Pub. Date: Dec. 1, 2022

(65) Prior Publication Data
US 2024/0164855 A1    May 23, 2024

(30) Foreign Application Priority Data

May 25, 2021 (CN) .......................... 202110573829.0

(51) Int. Cl.
*A61B 34/30* (2016.01)
*B25J 9/06* (2006.01)
*B25J 17/02* (2006.01)

(52) U.S. Cl.
CPC ................. *A61B 34/30* (2016.02); *B25J 9/06* (2013.01); *B25J 17/025* (2013.01); *A61B 2034/301* (2016.02)

(58) Field of Classification Search
CPC .............. A61B 34/30; A61B 2034/301; A61B 2034/302; A61B 34/00; B25J 9/06;
(Continued)

(56) References Cited

U.S. PATENT DOCUMENTS

2019/0365489 A1* 12/2019 Kasai ..................... A61B 1/055
2020/0146763 A1*  5/2020 Schena .................. A61B 34/30

FOREIGN PATENT DOCUMENTS

CN    102892363 A    1/2013
CN    109998685 A    7/2019
(Continued)

OTHER PUBLICATIONS

English Translation of WO-2020240940-A1 (Year: 2020).*

*Primary Examiner* — Victor L MacArthur
(74) *Attorney, Agent, or Firm* — Bret E. Field; Bozicevic, Field & Francis LLP

(57) ABSTRACT

This application provides a robotic arm and a control method therefor. The robotic arm comprises a spatial positioning mechanism, a planar motion mechanism and a connection and rotation joint connecting the spatial positioning mechanism and the planar motion mechanism. The space positioning mechanism comprises a base, and a joint mechanism including multiple joints, with the joint at a head end thereof installed onto the base, and the joint at a tail end rotatably connected to the connection and rotation joint; a tail end of the planar motion mechanism is connected to a surgical instrument. Perpendicular line of a plane where the planar motion mechanism is located is perpendicular to rotation axis of the connection and rotation joint; and the intersection between the rotation axis and axis of the surgical instrument is an active remote-center-of-motion point, which facilitates setting of the active remote-center-of-motion point and reduces occurrence of multi-arm collision.

13 Claims, 5 Drawing Sheets

(58) Field of Classification Search
CPC ...... B25J 17/025; B25J 9/1689; B25J 18/007;
B25J 18/00; B25J 9/16; B25J 17/00;
B25J 17/02; G05B 2219/45119
See application file for complete search history.

(56) References Cited

FOREIGN PATENT DOCUMENTS

| | | | |
|---|---|---|---|
| CN | 110680505 | A | 1/2020 |
| CN | 111227938 | A | 6/2020 |
| CN | 114098958 | A | 3/2022 |
| JP | 2005297187 | A | 10/2005 |
| WO | WO-2020240940 | A1 * | 12/2020 |

\* cited by examiner

MECHANICAL ARM AND CONTROL METHOD THEREFOR

CROSS-REFERENCE TO RELATED APPLICATION

This application is the national phase of International Application No. PCT/CN2022/085605, titled "MECHANICAL ARM AND CONTROL METHOD THEREFOR", filed on Apr. 7, 2022, which claims priority and right to Chinese patent application No. 202110573829.0 filed on May 25, 2021, which are incorporated herein by reference in their entirety.

FIELD OF THE INVENTION

The present invention relates to the technical field of medical devices, and in particular, to a robotic arm (also referred to as "mechanical arm") and a control method therefor.

BACKGROUND OF THE INVENTION

With constant developments of medical devices, computer technologies, and control technologies, minimally invasive surgery has been widely applied due to advantages such as less trauma, short recovery time, and less pain for patients. A robot for the minimally invasive surgery can avoid limitations in operation, such as hand tremor during a filtering operation, due to its high dexterity, high control accuracy, intuitive surgical images, and other characteristics, and is widely applied in abdominal cavity, pelvic cavity, thoracic cavity, and other surgical areas.

At present, the robot for the minimally invasive surgery includes a main operating arm and a robotic arm. The main operating arm collects operating signals of a doctor and processes the signals by using a control system to generate control signals for the robotic arm. The robotic arm performs surgical operations. During surgery of the robot, the robotic arm is clamped with a surgical instrument, which enters a body of a patient through a trocar inserted in an incision of a body surface of the patient. A point at which a centerline of a trocar axis intersects with the body surface is a "fixed point". Therefore, during the surgery, a surgical instrument rod needs to pass through this point through the trocar, thereby avoiding expanding a wound on the body surface of the patient or even causing surgical accidents. There are two manners for implementing the fixed point currently. The first manner is a mechanical fixed point. Based on a parallelogram linkage mechanism, a position of the fixed point is fixed relative to a position of a base. The trocar needs to be clamped onto the robotic arm to ensure that the position of the fixed point coincides with a position of the wound. However, a strict matching relationship needs to be met during the clamping process, bringing in high operational complexity and long preoperative preparation time. The second manner is an active remote-center-of-motion point. A universal industrial robot configuration is used, and an action control algorithm is used to constrain the surgical instrument so as to pass through a fixed point. However, a relatively complex kinematics inverse operation is required. Moreover, considering factors such as motion range of a joint and virtual constraint of the fixed point, singularity may be easily introduced. In addition, motion around the fixed point requires participation of various joints of the robotic arm, and when a plurality of arms are used in combination, interference among the plurality of arms may be easily caused.

SUMMARY OF THE INVENTION

In this regard, there is a need to provide a robotic arm and a control method therefor so as to resolve problems that a robotic arm as mentioned above has a complex kinematics inverse operation process and the plurality of arms thereof may interfere with each other.

A robotic arm is provided, which includes a spatial positioning mechanism, a planar motion mechanism, and a connection and rotation joint connecting the spatial positioning mechanism with the planar motion mechanism, wherein the spatial positioning mechanism includes a base and a joint mechanism, the joint mechanism includes a plurality of joints that are mounted sequentially, wherein, the joint at a head end of the joint mechanism is mounted onto the base, and the joint at a tail end of the joint mechanism is rotatably connected to the connection and rotation joint;

a tail end of the planar motion mechanism is connected to a surgical instrument, and a perpendicular line of a plane where the planar motion mechanism is located is perpendicular to a rotation axis of the connection and rotation joint; and a point at which the rotation axis of the connection and rotation joint intersects with an axis of the surgical instrument is an active remote-center-of-motion point.

In the robotic arm described above, the joints of the joint mechanism move relative to the base to drive the connection and rotation joint, the planar motion mechanism, and the surgical instrument to rotate accordingly, such that the connection and rotation joint, the planar motion mechanism, and the surgical instrument move in a wide range within a space. In this way, the active remote-center-of-motion point is positioned in a wide range within a space. The planar motion mechanism moves in a plane perpendicular to a direction of the rotation axis of the connection and rotation joint to drive the surgical instrument to move accordingly, such that the active remote-center-of-motion point moves in a plane where the planar motion mechanism is located. In this way, the active remote-center-of-motion point is positioned precisely in the plane where the planar motion mechanism is located. After the active remote-center-of-motion point is determined, the connection and rotation joint rotates around its rotation axis to drive the planar motion mechanism and the surgical instrument to rotate accordingly, such that when it is ensured that the active remote-center-of-motion point remains stationary, the surgical instrument performs a single-degree-of-freedom rotation around the active remote-center-of-motion point by taking the rotation axis of the connection and rotation joint as a rotation axis. The planar motion mechanism rotates, driving the surgical instrument to rotate accordingly, and therefore when it is ensured that the active remote-center-of-motion point remains stationary, the surgical instrument performs a single-degree-of-freedom rotation around the active remote-center-of-motion point by taking a direction perpendicular to the rotation axis of the connection and rotation joint as the rotation axis. Because the rotation of the surgical instrument around the active remote-center-of-motion point can be implemented without requiring the spatial positioning mechanism to move, collision risk that may occur when a plurality of arms move cooperatively are reduced. Moreover, by defining the point at which the rotation axis of the connection and rotation joint intersects with the axis of the surgical instrument as the active remote-center-of-motion point, setting of the active remote-center-of-motion point can be conveniently completed. Infinite solutions to the same posture of the surgical instrument can be implemented through linkage actions of the spatial positioning mechanism, the planar motion mechanism, and the connection and rotation joint, making the kinematics solution process simple.

In an embodiment, the joint mechanism includes at least two rotating joints, and a rotation axis of at least one of the rotating joints is perpendicular to the rotation axis of the connection and rotation joint.

In an embodiment, the joint mechanism includes two rotating joints and one moving joint, the moving joint is disposed between the two rotating joints or between the rotating joint and the base, a movement direction of the moving joint is parallel to the rotation axis of one of the rotating joints, and rotation axes of the two rotating joints are perpendicular to each other.

In an embodiment, the spatial positioning mechanism further includes three links, the base and an adjacent link, and adjacent links of the three links, are connected to each other via the moving joint or the rotating joint, and a link of the three links that is farthest to the base is connected to the planar motion mechanism via the connection and rotation joint.

In an embodiment, the joint mechanism includes three rotating joints that are mounted sequentially, wherein the rotating joint farthest to the connection and rotation joint is mounted on the base, rotation axes of two rotating joints that are close to the base are perpendicular to each other, and rotation axes of two rotating joint that are away from the base are parallel to each other.

In an embodiment, the spatial positioning mechanism further includes three links, the base and an adjacent link, and adjacent links of the three links, are connected to each other via the rotating joints, and a link of the three links that is farthest to the base is connected to the planar motion mechanism via the connection and rotation joint.

In an embodiment, the joint mechanism includes two rotating joints and two moving joints, wherein the two moving joints are disposed to be adjacent to each other, and movement directions of the two moving joints are perpendicular to each other and are parallel to a rotation axis of one of the rotating joints; one of the rotating joints is disposed between one side of the two moving joints and the base, and the other rotating joint is disposed at another side; and rotation axes of the two rotating joints are perpendicular to each other.

In an embodiment, the spatial positioning mechanism further includes four links, the base and an adjacent link, and adjacent links of the four links, are connected to each other via the moving joint or the rotating joint, and a link of the four links that is farthest to the base is connected to the planar motion mechanism via the connection and rotation joint.

In an embodiment, the planar motion mechanism includes four links and three rotating joints, wherein the four links are disposed sequentially, and two adjacent links are connected via one of the rotating joints; one of the four links at an edge position is connected to a tail end of the spatial positioning mechanism through the connection and rotation joint, and another link at an edge position is connected to the surgical instrument; and rotation axes of the three rotating joints are parallel to each other, and are all perpendicular to the rotation axis of the connection and rotation joint.

In an embodiment, action control of the active remote-center-of-motion point satisfies the following constraint relationships:

$$\gamma = \arccos\left(\frac{b^2 + c^2 + e^2}{2bc}\right);$$

$$\beta = \arccos\left(\frac{a^2 + e^2 - d^2}{2ae}\right) + \arccos\left(\frac{b^2 + e^2 - c^2}{2be}\right); \text{ and}$$

$$e = \sqrt{a^2 + d^2 - 2ad * \cos\alpha}.$$

Wherein, $\alpha$, $\beta$, and $\gamma$ sequentially represent angles formed by two adjacent links from a head end to the tail end of the planar motion mechanism; a represents a straight-line distance between center points of rotation of the first planar rotating joint and the second planar rotating joint, b represents a straight-line distance between center points of rotation of the second planar rotating joint and the third planar rotating joint, c represents a straight-line distance between the center point of rotation of the third planar rotating joint and the active remote-center-of-motion point, and d represents a straight-line distance between the center point of rotation of the first planar rotating joint and the active remote-center-of-motion point.

In an embodiment, the planar motion mechanism includes three sequentially disposed links, a slider, and two rotating joints. Wherein the slider is connected to one of the rotating joints to be an integral piece; another rotating joint is respectively connected to two adjacent links; the link connected to the slider is directly connected to the connection and rotation joint or is indirectly connected to the surgical instrument; and rotation axes of the two rotating joints are parallel to each other, and are both perpendicular to the rotation axis of the connection and rotation joint and a movement direction of the slider.

In an embodiment, the tail end of the planar motion mechanism is connected to the surgical instrument via a moving joint; and a movement direction of the moving joint is perpendicular to the rotation axis of the connection and rotation joint.

In an embodiment, the robotic arm further includes a laser generation module that is disposed on the planar motion mechanism. The laser generation module is coaxially disposed with the connection and rotation joint, and is configured to generate a laser to illuminate a positioning mark on the surgical instrument so as to indicate the active remote-center-of-motion point.

In addition, the present application further provides a control method for the robotic arm according to any one of the foregoing technical solutions, including:

controlling a spatial positioning mechanism to move, so as to enable a rotation axis of a connection and rotation joint to pass through a trocar orifice;

controlling a planar motion mechanism to move, so as to enable an axis of a surgical instrument to pass through the trocar orifice; and controlling a connection and rotation joint and the planar motion mechanism to move, so as to operate the surgical instrument around an active remote-center-of-motion point.

In the foregoing control method for the robotic arm, firstly, by controlling joints of the joint mechanism of the spatial positioning mechanism to move relative to the base so as to drive the connection and rotation joint, the planar motion mechanism and the surgical instrument to rotate accordingly, the connection and rotation joint, the planar motion mechanism and the surgical instrument are movable in a wide range within a space, to thereby achieve a large-scale positioning of the active remote-center-of-motion point within the space such that the rotation axis of the connection and rotation joint passes through the trocar orifice. Then, by controlling the movement of the planar motion mechanism such that it moves in a plane perpendicular to a direction of the rotation axis of the connection and rotation joint, the surgical instrument is driven to move accordingly such that the active remote-center-of-motion point moves in the plane where the planar motion mechanism is located. In this way, the active remote-center-of-motion point is positioned precisely in the plane where the planar motion mechanism is located, and the axis of the surgical instrument passes through the trocar orifice. Finally, the connection and rotation joint is controlled to rotate, the connection and rotation joint is rotated around the rotation axis of the connection and rotation joint, driving the planar motion mechanism and the surgical instrument to rotate accordingly, such that, when it is ensured that the active remote-center-of-motion point remains stationary, the surgical instrument performs a single-degree-of-freedom rotation around the active remote-center-of-motion point by taking the rotation axis of the connection and rotation joint as a rotation axis. The planar motion mechanism is controlled to rotate, driving the surgical instrument to rotate accordingly, such that, when it is ensured that the active remote-center-of-motion point remains stationary, the surgical instrument performs a single-degree-of-freedom rotation around the active remote-center-of-motion point by taking a direction perpendicular to the rotation axis of the connection and rotation joint as the rotation axis. According to the foregoing control method for the robotic arm, a fixed point can be positioned conveniently and accurately. Moreover, it is ensured that the rotation of the surgical instrument around the active remote-center-of-motion point can be implemented without movement of the spatial positioning mechanism, thereby reducing occurring of collisions when a plurality of arms move cooperatively.

In an embodiment, when a tail end of the planar motion mechanism of the robotic arm is connected to the surgical instrument through a moving joint, after controlling the connection and rotation joint and the planar motion mechanism to move, the method further includes:

controlling the moving joint to move to operate the surgical instrument through the active remote-center-of-motion point.

Figure 1:
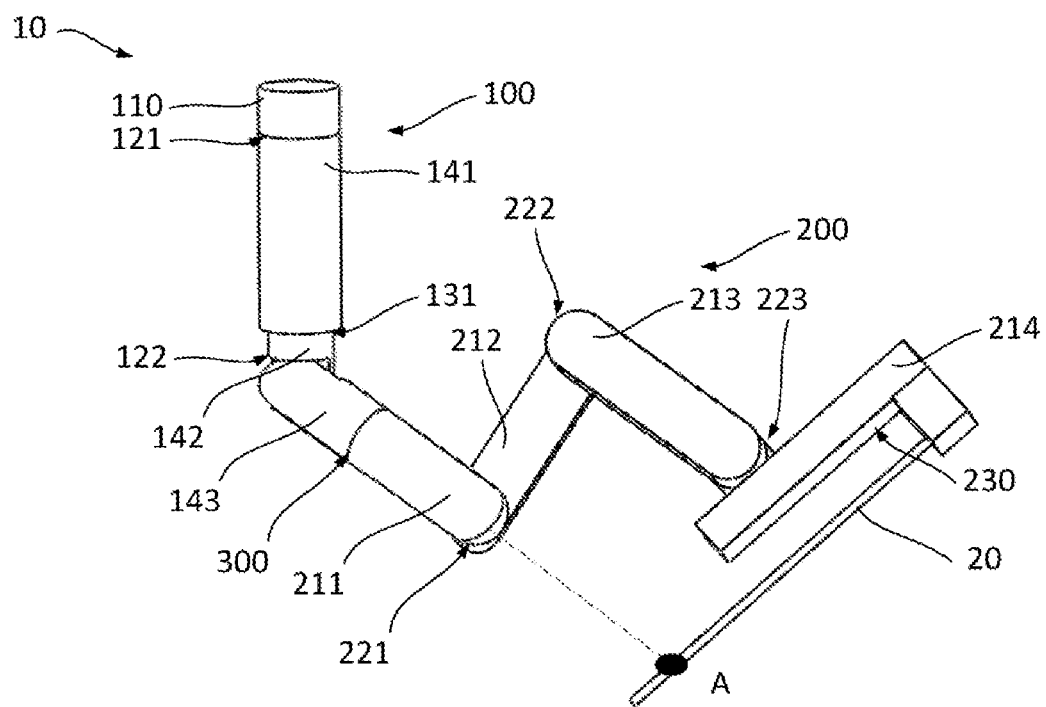
FIG. 1 is a structural schematic diagram of a structure of a robotic arm according to the present invention.

REFERENCE NUMERALS 10. robotic arm;
A. active remote-center-of-motion point;
100. spatial positioning mechanism; 110. base; 121. first rotating joint; 122. second rotating joint; 123. third rotating joint; 124. fourth rotating joint; 125. fifth rotating joint; 126. sixth rotating joint; 127. seventh rotating joint; 131. first moving joint; 132. second moving joint; 133. third moving joint; 141. first link; 142. second link; 143. third link; 144. fourth link; 145. fifth link; 146. sixth link; 147. seventh link; 148. eighth link; 149. ninth link; 150. tenth link;
200. planar motion mechanism; 211. first planar link; 212. second planar link; 213. third planar link; 214. fourth planar link; 215. fifth planar link; 216. sixth planar link; 217. seventh planar link; 221. first planar rotating joint; 222. second planar rotating joint; 223. third planar rotating joint; 224. fourth planar rotating joint; 225. fifth planar rotating joint; 230. first planar moving joint; 240. slider;
300. connection and rotation joint;
20. surgical instrument.

DETAILED DESCRIPTION OF THE EMBODIMENTS

To make the foregoing objectives, characteristics, and advantages of the present invention more apparent and easier to be understood, specific implementations of the present invention are described in detail herein with reference to the figures. Many specific details are described in the following description to facilitate full understanding of the present invention. However, the present invention may be implemented in many other ways different from those described herein, and a person skilled in the art may make similar improvements without departing from the connotation of the present invention. Therefore, the present invention is not limited to specific embodiments disclosed below.

It should be understood that, in the description of the present invention, orientations or positional relationships indicated with such terms as "center", "longitudinal", "transverse", "length", "width", "thickness", "up", "down", "front", "back", "left", "right", "vertical", "horizontal", "top", "bottom", "inside", "outside", "clockwise", "counterclockwise", "axial", "radial" are based on the orientations or positional relationship depicted in the figures, and are merely for convenience of describing the present invention and for simplifying the description, rather than indicating or implying that a device or an element referred to must have a particular orientation or be constructed and operated in a particular orientation. Therefore, these should not be construed as limitations to the present invention.

Besides, the terms "first" and "second" are merely used for description, and shall not be understood as an indication or implication of relative importance or implicit indication of the quantity of the technical features referred to by these terms. Therefore, a feature referred to by "first" or "second"

may explicitly or implicitly includes at least one feature. In the description of the present invention, "a plurality of" means at least two, such as two or three, unless otherwise specified.

It should also be noted that, in the present invention, unless otherwise specified and defined, the terms such as "mount", "connected", "connect", and "fixed" should be broadly understood. For example, it may be a fixed connection, a detachable connection, or an integrated connection; it may be a mechanical connection or an electrical connection; it may be directly connected, or be indirectly connected through an intermediate medium; or it may be internal communication between two elements or an interaction relationship between two elements, unless otherwise specified. For a person of ordinary skills in the art, specific meanings of the foregoing terms in the present invention can be understood according to specific conditions.

In the present invention, unless otherwise specified and limited, if a first feature is described to be "above" or "below" a second feature, it may mean that the first feature is in direct contact with the second feature, or the first feature is in indirect contact with the second feature through an intermediate medium. Moreover, if the first feature is described to be "over", "above", and "on" the second feature, it may mean that the first feature is directly or diagonally above the second feature, or merely indicates that a horizontal level of the first feature is higher than that of the second feature. If the first feature is described to be "under", "below", and "beneath" the second feature, it may mean that the first feature is directly or diagonally below the second feature, or merely indicates that a horizontal level of the first feature is lower than that of the second feature.

It should be noted that, when an element is referred to as being "fixed" or "disposed" on another element, it may be directly on another element, or there may be an intermediate element. When an element is referred to as being "connected to" another element, it may be directly connected to another element or an intermediate element may also exist. The terms "perpendicular", "horizontal", "above", "below", "left", and "right" and similar expressions used herein are for illustrative purposes only and do not mean the only implementation.

The technical solutions provided according to the embodiments of the present invention will be described herein with reference to the accompanying drawings. As shown in FIG. 1, the present invention provides a robotic arm 10 that is applied to a robot for minimally invasive surgery. A surgical instrument 20 is detachably connected to a tail end of the robotic arm 10. In this way, an active remote-center-of-motion point A can be positioned before surgery, and the surgical instrument 20 can be driven to pass through the active remote-center-of-motion point A to perform surgical operations during surgery. The robotic arm 10 includes three parts, that is, a spatial positioning mechanism 100, a planar motion mechanism 200, and a connection and rotation joint 300. The connection and rotation joint 300 connects the spatial positioning mechanism 100 and the planar motion mechanism 200.

The spatial positioning mechanism 100 includes a base 110 and a joint mechanism including a plurality of joints. A quantity of the joints may be two, three, or more. The plurality of joints are sequentially mounted to the base 110, wherein, the joint at a head end of the joint mechanism may be directly connected to the base 110, and the joint at a tail end of the joint mechanism is rotatably connected to the connection and rotation joint 300.

A tail end of the planar motion mechanism 200 is connected to the surgical instrument 20, and a perpendicular line of a plane where the planar motion mechanism 200 is located is perpendicular to a rotation axis of the connection and rotation joint 300.

A point at which the rotation axis of the connection and rotation joint 300 intersects with an axis of the surgical instrument 20 is the active remote-center-of-motion point A. The rotation axis of the connection and rotation joint 300 always passes through the active remote-center-of-motion point A during the surgery.

In the robotic arm 10 described above, the joints of the joint mechanism move relative to the base 110 to drive the connection and rotation joint 300, the planar motion mechanism 200, and the surgical instrument 20 to rotate accordingly, such that the connection and rotation joint 300, the planar motion mechanism 200, and the surgical instrument 20 can move in a wide range in space. In this way, the active remote-center-of-motion point A can be positioned in a wide range in the space. The tail end of the planar motion mechanism 200 is described with reference to a position of a moving joint connected to the surgical instrument 20 in the accompanying drawings. That the tail end of the planar motion mechanism 200 is connected to the surgical instrument 20 means that the moving joint located at the tail end of the planar motion mechanism 200 is connected to the surgical instrument 20. The planar motion mechanism 200 moves in a plane perpendicular to a direction of the rotation axis of the connection and rotation joint 300 to drive the surgical instrument 20 to move accordingly, such that the active remote-center-of-motion point A moves in the plane where the planar motion mechanism 200 is located. In this way, the active remote-center-of-motion point A is positioned precisely in the plane where the planar motion mechanism 200 is located. The connection and rotation joint 300 rotates around the rotation axis thereof, driving the planar motion mechanism 200 and the surgical instrument 20 to rotate together with it, and therefore the surgical instrument 20 performs single-degree-of-freedom rotation around the active remote-center-of-motion point A by taking the rotation axis of the connection and rotation joint 300 as a rotation axis, when it is ensured that the active remote-center-of-motion point A remains stationary. The planar motion mechanism 200 rotates to drive the surgical instrument 20 to rotate accordingly, such that when it is ensured that the active remote-center-of-motion point A remains stationary, the surgical instrument 20 performs single-degree-of-freedom rotation around the active remote-center-of-motion point A by taking a direction perpendicular to the rotation axis of the connection and rotation joint 300 as the rotation axis. Because the rotation of the surgical instrument 20 around the active remote-center-of-motion point A can be implemented without requiring the spatial positioning mechanism 100 to move, collisions which may occur when a plurality of arms move in combination are reduced. Moreover, by defining the point at which the rotation axis of the connection and rotation joint 300 intersects with the axis of the surgical instrument 20 as the active remote-center-of-motion point A, setting of the active remote-center-of-motion point A can be conveniently made. Infinite solutions to the same posture of the surgical instrument 20 can be implemented through linkage actions of the spatial positioning mechanism 100, the planar motion mechanism 200, and the connection and rotation joint 300, making the kinematics solution process simple.

Figure 2:
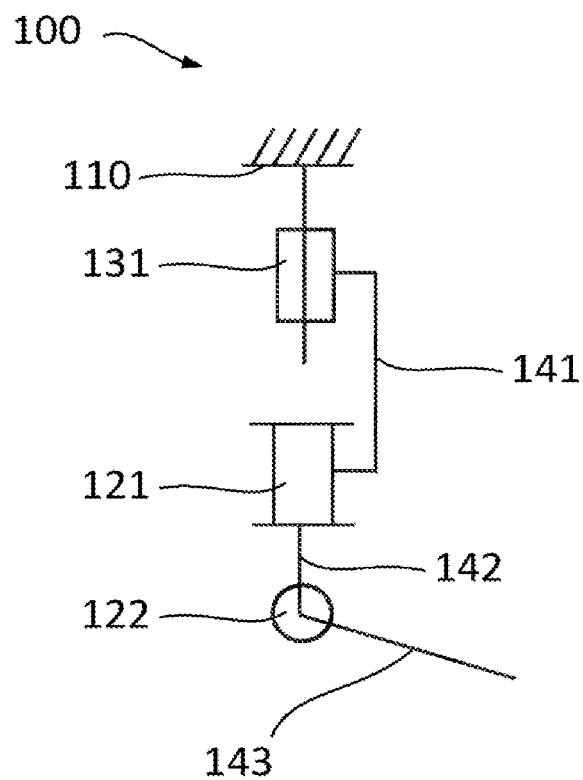
FIG. 2 is a schematic diagram of a spatial positioning mechanism in a robotic arm according to the present invention.

The spatial positioning mechanism 100 may have various structural forms. In a preferred implementation, as shown in FIG. 1 and FIG. 2, the joint mechanism includes at least two rotating joints. A rotation axis of at least one of the rotating joints is perpendicular to the rotation axis of the connection and rotation joint 300. In certain settings, a quantity of the rotating joints may be two, three, or more, among which, a rotation axis of one rotating joint may be perpendicular to the rotation axis of the connection and rotation joint 300, or rotation axes of two rotating joints may be perpendicular to the rotation axis of the connection and rotation joint 300.

In the robotic arm 10 described above, the joint mechanism includes at least two rotating joints, which move respectively to drive the connection and rotation joint 300, the planar motion mechanism 200, and the surgical instrument 20 to rotate accordingly, such that the connection and rotation joint 300, the planar motion mechanism 200, and the surgical instrument 20 move in a wide range in the space. It is defined that the rotation axis of at least one of the rotating joints is perpendicular to the rotation axis of the connection and rotation joint 300, such that the connection and rotation joint 300, the planar motion mechanism 200, and the surgical instrument 20 can be driven to rotate along a rotation axis perpendicular to the rotation axis of the connection and rotation joint 300. In this way, it helps to control the connection and rotation joint 300, the planar motion mechanism 200, and the surgical instrument 20 to move in a wide range in the space. Certainly, rotation axes of the at least two rotating joints may also not be perpendicular to the rotation axis of the connection and rotation joint 300. Moreover, the rotation axes of the at least two rotating joints may be set based on actual situation of the robotic arm 10.

The joint mechanism may have various structural forms. In a preferred implementation, the joint mechanism includes two rotating joints and one moving joint. As shown in FIG. 1, the joint mechanism includes a first rotating joint 121, a second rotating joint 122, and a first moving joint 131. A rotation axis of the first rotating joint 121 is perpendicular to that of the second rotating joint 122. The first moving joint 131 is disposed between the first rotating joint 121 and the second rotating joint 122. A movement direction of the first moving joint 131 is parallel to the rotation axis of the first rotating joint 121. As shown in FIG. 2, the joint mechanism includes a first rotating joint 121, a second rotating joint 122, and a first moving joint 131. A rotation axis of the first rotating joint 121 is perpendicular to that of the second rotating joint 122. The first moving joint 131 is disposed between the base 110 and the first rotating joint 121. A movement direction of the first moving joint 131 is parallel to the rotation axis of the first rotating joint 121. In specific setting, the movement direction of the first moving joint 131 may completely coincide with the rotation axis of the first rotating joint 121, the movement direction of the first moving joint 131 may alternatively be disposed to be parallel to and offset with respect to the rotation axis of the first rotating joint 121.

In the robotic arm 10 described above, the first rotating joint 121, the first moving joint 131, and the second rotating joint 122 are mounted onto the base 110. The movement direction of the first moving joint 131 is parallel to the rotation axis of the first rotating joint 121. The rotation axis of the first rotating joint 121 is perpendicular to that of the second rotating joint 122. Moreover, the first rotating joint 121 and the second rotating joint 122 are respectively perpendicular to the rotation axis of the connection and rotation joint 300. When the spatial positioning mechanism 100 moves, rotation movements of the first rotating joint 121 and the second rotating joint 122 can make the spatial positioning mechanism 100 rotate in two directions perpendicular to the rotation axis of the connection and rotation joint 300, to drive the connection and rotation joint 300, the planar motion mechanism 200, and the surgical instrument 20 to rotate accordingly. In this way, the active remote-center-of-motion point A can rotate by taking two directions perpendicular to the rotation axis of the connection and rotation joint 300 as rotation axes. Movement of the first moving joint 131 can make the spatial positioning mechanism 100 move in a direction perpendicular to the rotation axis of the connection and rotation joint 300, to drive the connection and rotation joint 300, the planar motion mechanism 200, and the surgical instrument 20 to move accordingly. In this way, the active remote-center-of-motion point A can move in a direction perpendicular to the rotation axis of the connection and rotation joint 300. Therefore, by configuring the spatial positioning mechanism 100 to have the first rotating joint 121, the second rotating joint 122, and the first moving joint 131 as described above, the active remote-center-of-motion point A can be conveniently and quickly positioned in a large range in the space. Moreover, the configuration is simple and is easy for action control. Of course, the rotation axis of the first rotating joint 121 may not be perpendicular to that of the second rotating joint 122. Moreover, the rotation axes of the first rotating joint 121 and the second rotating joint 122 may not be perpendicular to the rotation axis of the connection and rotation joint 300. Setting manners for the rotation axes of the first rotating joint 121 and the second rotating joint 122 and for the movement direction of the first moving joint 131 may base on actual situation of the robotic arm 10.

Specifically, as shown in FIG. 1 and FIG. 2, the spatial positioning mechanism 100 includes three links: a first link 141, a second link 142, and a third link 143. The base 110 and one adjacent link, and adjacent links of the three links, are respectively connected to each other with a moving joint or a rotating joint. The third link 143 of the three links that is farthest to the base 110 is connected to the planar motion mechanism 200 via the connection and rotation joint 300. As shown in FIG. 1, the base 110 is connected to the first link 141 via the first rotating joint 121, the first link 141 is connected to the second link 142 via the first moving joint 131, and the second link 142 is connected to the third link 143 via the second rotating joint 122. As shown in FIG. 2, the base 110 is connected to the first link 141 via the first moving joint 131, the first link 141 is connected to the second link 142 via the first rotating joint 121, and the second link 142 is connected to the third link 143 via the second rotating joint 122.

In the robotic arm 10 described above, as shown in FIG. 1, when the spatial positioning mechanism 100 moves, the first rotating joint 121 rotates to drive the first link 141 to rotate, causing the first moving joint 131, the second link 142, the second rotating joint 122, and the third link 143 that are directly or indirectly connected to the first link 141 rotate accordingly. The third link 143 drives the connection and rotation joint 300, the planar motion mechanism 200, and the surgical instrument 20 that are directly or indirectly connected thereto to rotate accordingly, such that the active remote-center-of-motion point A can rotate by taking a first direction perpendicular to the rotation axis of the connection and rotation joint 300 as a rotation axis. The first moving joint 131 moves, driving the second link 142 to move accordingly, which in turn drives the second rotating joint 122 and the third link 143 that are directly or indirectly connected to the second link 142 to move accordingly, and further, the third link 143 drives the connection and rotation joint 300, the planar motion mechanism 200, and the surgical instrument 20 that are directly or indirectly connected to the third link to move accordingly, which enables the active remote-center-of-motion point A to move in a first direction perpendicular to the rotation axis of the connection and rotation joint 300. The second rotating joint 122 rotates, driving the third link 143 to rotate, and the third link 143 in turn drives the connection and rotation joint 300, the planar motion mechanism 200, and the surgical instrument 20 that are directly or indirectly connected thereto to rotate accordingly, therefore causing the active remote-center-of-motion point A to rotate by taking a second direction perpendicular to the rotation axis of the connection and rotation joint 300 as a rotation axis. The first direction is perpendicular to the second direction, which enables the active remote-center-of-motion point A to rotate by taking the two directions perpendicular to the rotation axis of the connection and rotation joint 300 as rotation axes.

As shown in FIG. 2, when the spatial positioning mechanism 100 moves, the first rotating joint 131 moves, driving the first link 141 to move, which drives the first rotating joint 121, the second link 142, the second rotating joint 122, the third link 143, the connection and rotation joint 300, the planar motion mechanism 200, and the surgical instrument 20 that are directly or indirectly connected to the first link 141 to move accordingly, and thus causing the active remote-center-of-motion point A to move in a first direction perpendicular to the rotation axis of the connection and rotation joint 300. The first rotating joint 121 rotates, driving the second link 142 to rotate accordingly, which in turn drives the second rotating joint 122, the third link 143, the connection and rotation joint 300, the planar motion mechanism 200, and the surgical instrument 20 that are directly or indirectly connected to the second link 142 to rotate accordingly, and therefore causing the active remote-center-of-motion point A to rotate by taking the first direction perpendicular to the rotation axis of the connection and rotation joint 300 as a rotation axis. The second rotating joint 122 rotates to drive the third link 143 to rotate accordingly. The third link 143 drives the connection and rotation joint 300, the planar motion mechanism 200, and the surgical instrument 20 that are directly or indirectly connected thereto to rotate accordingly, such that the active remote-center-of-motion point A rotates by taking a second direction perpendicular to the rotation axis of the connection and rotation joint 300 as a rotation axis. The first direction is perpendicular to the second direction, which enables the active remote-center-of-motion point A to rotate by taking the two directions perpendicular to the rotation axis of the connection and rotation joint 300 as rotation axes.

Figure 3:
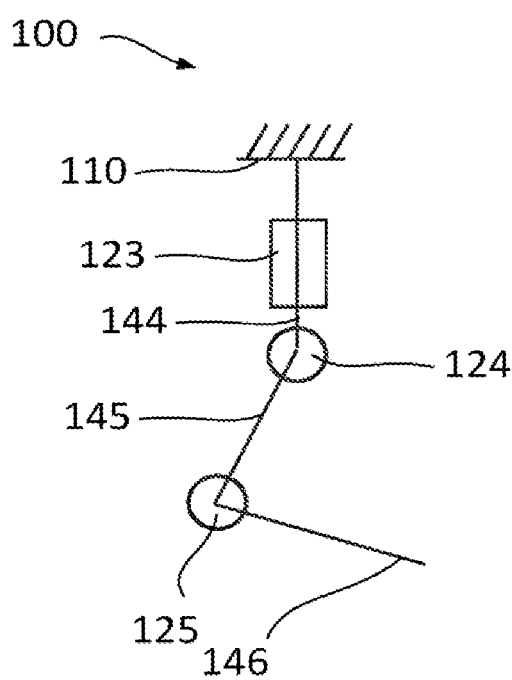
FIG. 3 is a schematic diagram of another spatial positioning mechanism in a robotic arm according to the present invention.

The spatial positioning mechanism 100 may have various structural forms. In a preferred implementation, as shown in FIG. 3, the joint mechanism includes three joints: a third rotating joint 123, a fourth rotating joint 124, and a fifth rotating joint 125. The third rotating joint 123, the fourth rotating joint 124, and the fifth rotating joint 125 are mounted sequentially, wherein the third rotating joint 123 of the three joints that is farthest to the connection and rotation joint 300 is mounted onto the base 110, rotation axes of the third rotating joint 123 and the fourth rotating joint 124 of the three joints that are close to the base 110 are perpendicular to each other, and rotation axes of the fourth rotating joint 124 and the fifth rotating joint 125 of the three joints that are away from the base 110 are parallel to each other.

As shown in FIG. 3, in one specific embodiment, the spatial positioning mechanism 100 further includes three links, that is, a fourth link 144, a fifth link 145, and a sixth link 146. The base 110 and one adjacent link, and adjacent links of the three links, are respectively connected to each other via the rotating joints. Moreover, the sixth link 146 of the three links that is farthest to the base 110 is connected to the planar motion mechanism 200 through the connection and rotation joint 300. In one specific setting, the base 110 is connected to the fourth link 144 through the third rotating joint 123, the fourth link 144 is connected to the fifth link 145 through the fourth rotating joint 124, and the fifth link 145 is connected to the sixth link 146 through the fifth rotating joint 125.

In the robotic arm 10 described above, when the spatial positioning mechanism 100 moves, rotation movements of the third rotating joint 123 and the fourth rotating joint 124 can make the spatial positioning mechanism 100 rotate by taking two directions perpendicular to the rotation axis of the connection and rotation joint 300 as rotation axes, to drive the connection and rotation joint 300, the planar motion mechanism 200, and the surgical instrument 20 to rotate accordingly, which enables the active remote-center-of-motion point A to rotate by taking the two directions perpendicular to the rotation axis of the connection and rotation joint 300 as rotation axes. Rotation of the fifth rotating joint 125 can make the spatial positioning mechanism 100 rotate by taking a direction perpendicular to the rotation axis of the connection and rotation joint 300 as a rotation axis, to drive the connection and rotation joint 300, the planar motion mechanism 200, and the surgical instrument 20 to rotate accordingly. In this way, the active remote-center-of-motion point A can rotate in a direction perpendicular to the rotation axis of the connection and rotation joint 300. Therefore, by configuring the spatial positioning mechanism 100 to have the foregoing three joints, the active remote-center-of-motion point A can be conveniently and quickly positioned in a large range within a space. Moreover, the configuration is simple and is easy for action control. Certainly, the rotation axis of the third rotating joint 123 may not be perpendicular to that of the fourth rotating joint 124. Moreover, the rotation axes of the third rotating joint 123 and the fourth rotating joint 124 may not be perpendicular to the rotation axis of the connection and rotation joint 300. Besides, setting manners for the rotation axes of the third rotating joint 123, the fourth rotating joint 124, and the fifth rotating joint 125 may base on actual situation of the robotic arm 10.

Figure 4:
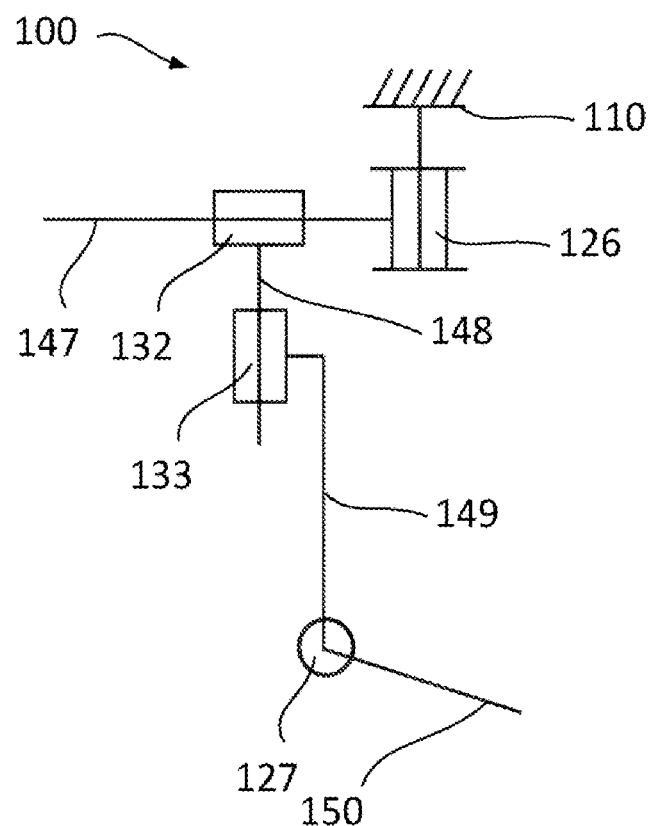
FIG. 4 is a schematic diagram of still another spatial positioning mechanism in a robotic arm according to the present invention.

The spatial positioning mechanism 100 may have various structural forms. As shown in FIG. 4, in a preferred implementation, the joint mechanism 120 includes: two rotating joints, that is, a sixth rotating joint 126 and a seventh rotating joint 127; and two moving joints, that is, a second moving joint 132 and a third moving joint 133. The second moving joint 132 is disposed adjacent to the third moving joint 133. Moreover, a movement direction of the second moving joint 132 is perpendicular to that of the third moving joint 133, while the movement direction of the third moving joint 133 is parallel to a rotation axis of the sixth rotating joint 126. The sixth rotating joint 126 is disposed between one side of the second moving joint 132 and the third moving joint 133 and the base 110, and the seventh rotating joint 127 is disposed at another side of the second moving joint 132 and the third moving joint 133. A rotation axis of the sixth rotating joint 126 is perpendicular to that of the seventh rotating joint 127.

Specifically, as shown in FIG. 4, the spatial positioning mechanism 100 further includes four links: a seventh link 147, an eighth link 148, a ninth link 149, and a tenth link 150. Adjacent two of the base 110 and the four links are connected to each other via a moving joint or a rotating joint, respectively. Moreover, the tenth link 150 of the four links that is farthest to the base 110 is connected to the planar motion mechanism 200 via the connection and rotation joint 300. In the specific setting, the base 110 is connected to the seventh link 147 via the sixth rotating joint 126, the seventh link 147 is connected to the eighth link 148 via the second moving joint 132, the eighth link 148 is connected to the ninth link 149 via the third moving joint 133, and the ninth link 149 is connected to the tenth link 150 via the seventh rotating joint 127.

With the robotic arm 10 described above, when the spatial positioning mechanism 100 moves, rotation movements of the sixth rotating joint 126 and the seventh rotating joint 127 can enable the spatial positioning mechanism 100 to rotate by taking a direction perpendicular to the rotation axis of the connection and rotation joint 300 as a rotation axis, to drive the connection and rotation joint 300, the planar motion mechanism 200, and the surgical instrument 20 to rotate accordingly, which therefore enables the active remote-center-of-motion point A to rotate by taking two directions perpendicular to the rotation axis of the connection and rotation joint 300 as rotation axes. Movements of the second moving joint 132 and the third moving joint 133 can enable the spatial positioning mechanism 100 to move in a direction perpendicular to the rotation axis of the connection and rotation joint 300, to drive the connection and rotation joint 300, the planar motion mechanism 200, and the surgical instrument 20 to move accordingly, which therefore enables the active remote-center-of-motion point A to move in a direction perpendicular to the rotation axis of the connection and rotation joint 300. Therefore, by configuring the spatial positioning mechanism 100 to have the two rotating joints and the two moving joints that are described above, the active remote-center-of-motion point A can be conveniently and quickly positioned in a large range within a space. Moreover, the configuration is simple and is easy for action control. Certainly, the rotation axis of the sixth rotating joint 126 may not be perpendicular to that of the seventh rotating joint 127. Moreover, the movement direction of the second moving joint 132 may not be perpendicular to that of the third moving joint 133. Besides, setting manners for the rotation axes of the sixth rotating joint 126 and the seventh rotating joint 127, and for the movement directions of the second moving joint 132 and the third moving joint 133 may be determined based on actual situation of the robotic arm 10.

Figure 5:
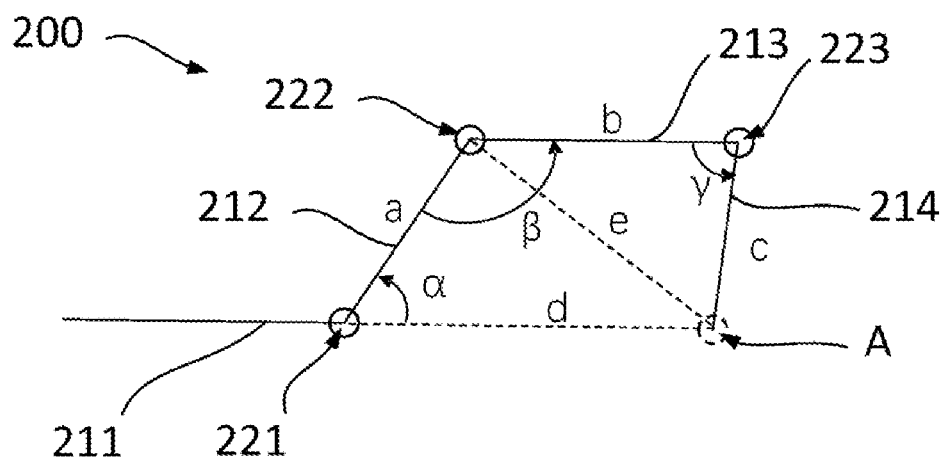
FIG. 5 is a schematic diagram of a planar motion mechanism in a robotic arm according to the present invention.

The planar motion mechanism 200 may have various structural forms. In a preferred implementation, as shown in FIG. 1 and FIG. 5, the planar motion mechanism 200 includes: four links, that is, a first planar link 211, a second planar link 212, a third planar link 213, and a fourth planar link 214; and three rotating joints, that is, a first planar rotating joint 221, a second planar rotating joint 222, and a third planar rotating joint 223. The first planar link 211, the second planar link 212, the third planar link 213, and the fourth planar link 214 are sequentially disposed, with two adjacent links being connected via a rotating joint. The first planar link 211 of the four links that is arranged at an edge position is connected to the tail end of the spatial positioning mechanism 100 via the connection and rotation joint 300, and the fourth planar link 214 of the four links that is arranged at another edge position is connected to the surgical instrument 20. Rotation axes of the first planar rotating joint 221, the second planar rotating joint 222, and the third planar rotating joint 223 are parallel to each other, and the first planar rotating joint 221, the second planar rotating joint 222, and the third planar rotating joint 223 are all perpendicular to the rotation axis of the connection and rotation joint 300. In the specific setting, the first planar link 211, the first planar rotating joint 221, the second planar link 212, the second planar rotating joint 222, the third planar link 213, the third planar rotating joint 223, and the fourth planar link 214 are sequentially connected.

Specifically, action control of the active remote-center-of-motion point A meets the following constraint relationships:

$$\gamma = a\cos\left(\frac{b^2 + c^2 + e^2}{2bc}\right);$$

$$\beta = a\cos\left(\frac{a^2 + e^2 - d^2}{2ae}\right) + a\cos\left(\frac{b^2 + e^2 - c^2}{2be}\right); \text{ and}$$

$$e = \sqrt{a^2 + d^2 - 2ad * \cos\alpha}.$$

Wherein, $\alpha$ represents an angle complementary to an angle formed by the first planar link 211 and the second planar link 212; $\beta$ represents an angle formed by the second planar link 212 and the third planar link 213; $\gamma$ represents an angle formed by the third planar link 213 and the fourth planar link 214; a represents a straight-line distance between center points of rotation of the first planar rotating joint 221 and the second planar rotating joint 222, b represents a straight-line distance between center points of rotation of the second planar rotating joint 222 and the third planar rotating joint 223, c represents a straight-line distance between the center point of rotation of the third planar rotating joint 223 and the active remote-center-of-motion point A, and d represents a straight-line distance between the center point of rotation of the first planar rotating joint 221 and the active remote-center-of-motion point A.

With the robotic arm 10 described above, when the planar motion mechanism 200 moves, the first planar rotating joint 221 rotates, driving the second planar link 212, the second planar rotating joint 222, the third planar link 213, the third planar rotating joint 223, the fourth planar link 214, and the surgical instrument 20 to rotate accordingly, to thereby drive the active remote-center-of-motion point A to rotate in a plane perpendicular to the rotation axis of the connection and rotation joint 300. The second planar rotating joint 222 rotates, driving the second planar link 212, the third planar link 213, the third planar rotating joint 223, the fourth planar link 214, and the surgical instrument 20 to rotate accordingly, which enables the active remote-center-of-motion point A to rotate in the plane perpendicular to the rotation axis of the connection and rotation joint 300. The third planar rotating joint 223 rotates, driving the second planar link 212, the second planar rotating joint 222, the third planar link 213, the third planar rotating joint 223, the fourth planar link 214, and the surgical instrument 20 to rotate accordingly, which enables the active remote-center-of-motion point A to rotate in the plane perpendicular to the rotation axis of the connection and rotation joint 300. Therefore, by configuring the planar motion mechanism 200 to have a planar four-rod mechanism as mentioned above, the active remote-center-of-motion point A can be conveniently and quickly positioned precisely in a plane where the planar motion mechanism 200 is located. Moreover, the configuration is simple and is easy for action control. After the active remote-center-of-motion point A is determined, combined action of the first planar rotating joint 221, the second planar rotating joint 222, and the third planar rotating joint 223 drives the planar motion mechanism 200 to rotate around the active remote-center-of-motion point A by taking a direction perpendicular to the rotation axis of the connection and rotation joint 300 as a rotation axis.

Specifically, to facilitate mounting of the surgical instrument 20, as shown in FIG. 1, the fourth planar link 214 is connected to the surgical instrument 20 through a first planar moving joint 230, and a movement direction of the first planar moving joint 230 is perpendicular to the rotation axis of the first planar rotating joint 221.

With the robotic arm 10 described above, by configuring the first planar moving joint 230 to be connected to the fourth planar link 214 and the surgical instrument 20, and the movement direction of the first planar moving joint 230 to be perpendicular to the rotation axis of the first planar rotating joint 221, when it is ensured that the active remote-center-of-motion point A remains stationary during surgery, movement of the surgical instrument 20 within a wound can be achieved by controlling the movement of the first planar moving joint 230, which facilitates surgical operations.

To facilitate positioning of the active remote-center-of-motion point A, in a preferred implementation, the robotic arm 10 further includes a laser generation module. The laser generation module is disposed on the first planar link 211 and is coaxial with the connection and rotation joint 300, and is configured to generate a laser to illuminate a positioning mark on the surgical instrument 20, so as to indicate the position of the active remote-center-of-motion point A.

In the robotic arm 10 as described above, the positioning mark is coated on a rod surface of the surgical instrument 20. The laser generation module emits a laser along a direction of the rotation axis of the connection and rotation joint 300, and a positioning mark area illuminated by the laser is the position for the active remote-center-of-motion point A. In this way, the active remote-center-of-motion point A can be easily and quickly identified.

Figure 6:
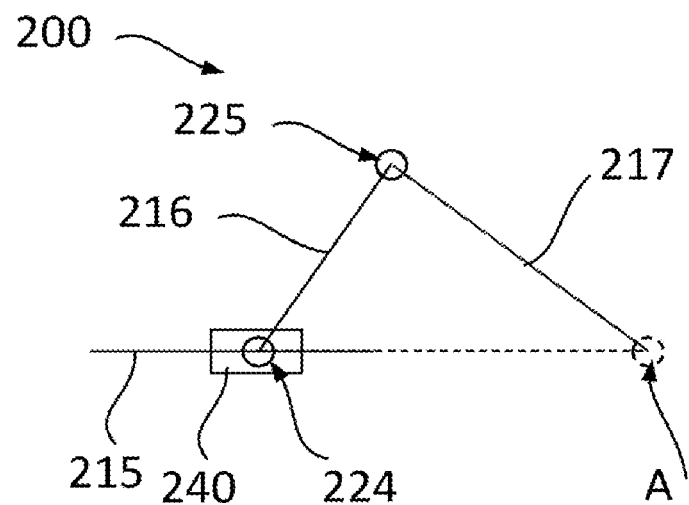
FIG. 6 is a schematic diagram of another planar motion mechanism in a robotic arm according to the present invention.

The planar motion mechanism 200 may have various structural forms. In a preferred implementation, as shown in FIG. 6, the planar motion mechanism 200 includes: three sequentially connected links, that is, a fifth planar link 215, a sixth planar link 216, and a seventh planar link 217; a slider 240; and two rotating joints, that is, a fourth planar rotating joint 224 and a fifth planar rotating joint 225. The slider 240 is integrally connected to the fourth planar rotating joint 224. The slider 240 is further connected to the fifth planar link 215 and is slidable along the fifth planar link 215. The fourth planar rotating joint 224 is connected to the sixth planar link 216. The fifth planar rotating joint 225 is connected to the adjacent sixth planar link 216 and the adjacent seventh planar link 217, respectively. The fifth planar link 215 may be directly connected to the connection and rotation joint 300. A rotation axis of the fourth planar rotating joint 224 is parallel to that of the fifth planar rotating joint 225. The rotation axes of the fourth planar rotating joint 224 and the fifth planar rotating joint 225 are perpendicular to the rotation axis of the connection and rotation joint 300. The rotation axes of the fourth planar rotating joint 224 and the fifth planar rotating joint 225 are perpendicular to a movement direction of the slider 240.

Figure 7:
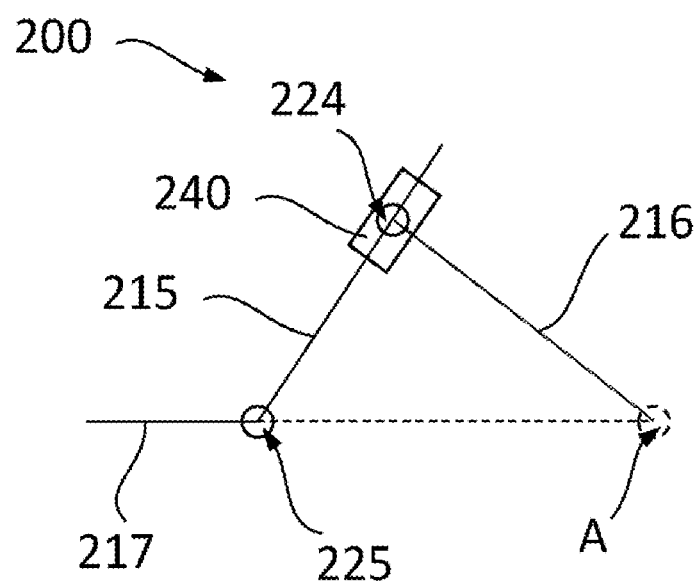
FIG. 7 is a schematic diagram of still another planar motion mechanism in a robotic arm according to the present invention.

As shown in FIG. 7, the planar motion mechanism 200 includes: three sequentially connected links, that is, a seventh planar link 217, a fifth planar link 215, and a sixth planar link 216; a slider 240; and two rotating joints, that is, a fourth planar rotating joint 224 and a fifth planar rotating joint 225. The slider 240 is connected to the fourth planar rotating joint 224 into an integral piece. The slider 240 is connected to the fifth planar link 215 and is slidable along the fifth planar link 215. The fourth planar rotating joint 224 is connected to the sixth planar link 216. The fifth planar rotating joint 225 is respectively connected to the adjacent sixth planar link 216 and the adjacent fifth planar link 215. The fifth planar link 215 may also be indirectly connected to the surgical instrument 20 through the sixth planar link 216, the slider 240, and the fourth planar rotating joint 224. A rotation axis of the fourth planar rotating joint 224 is parallel to that of the fifth planar rotating joint 225. The rotation axes of the fourth planar rotating joint 224 and the fifth planar rotating joint 225 are perpendicular to the rotation axis of the connection and rotation joint 300. The rotation axes of the fourth planar rotating joint 224 and the fifth planar rotating joint 225 are perpendicular to a movement direction of the slider 240.

In the robotic arm 10 described above, as shown in FIG. 6, when the planar motion mechanism 200 moves, the slider 240 slides, driving the fourth planar rotating joint 224, the sixth planar link 216, the fifth planar rotating joint 225, the seventh planar link 217, and the surgical instrument 20 to move accordingly, to enable the active remote-center-of-motion point A to move in a plane perpendicular to the rotation axis of the connection and rotation joint 300. The fifth planar rotating joint 225 rotates, driving the sixth planar link 216, the seventh planar link 217, and the surgical instrument 20 to move accordingly, so as to enable the active remote-center-of-motion point A to rotate in the plane perpendicular to the rotation axis of the connection and rotation joint 300. As shown in FIG. 7, the fifth planar rotating joint 225 rotates, driving the fifth planar link 215, the slider 240, the fourth planar rotating joint 224, the sixth planar link 216, and the surgical instrument 20 to move accordingly, enabling the active remote-center-of-motion point A to rotate in the plane perpendicular to the rotation axis of the connection and rotation joint 300. The slider 240 slides, driving the fourth planar rotating joint 224, the sixth planar link 216, and the surgical instrument 20 to move accordingly, to enable the active remote-center-of-motion point A to move in the plane perpendicular to the rotation axis of the connection and rotation joint 300. Therefore, with the configuration of the planar motion mechanism 200, the active remote-center-of-motion point A can be conveniently and quickly positioned precisely in a plane where the planar motion mechanism 200 is located. Moreover, the configuration is simple and is easy for action control. After the active remote-center-of-motion point A is determined, combined linkage action of the fourth planar rotating joint 224 and the fifth planar rotating joint 225 drives the planar motion mechanism 200 to rotate around the active remote-center-of-motion point A by taking a direction perpendicular to the rotation axis of the connection and rotation joint 300 as a rotation axis.

It should be noted that the rotating joints described above may be driven by motor-driven harmonic reducers, planetary reducers, RV reducers, or other gear transmissions; or may be directly driven by DD motors. The moving of the moving joints described above may be implemented by lifting of a lead screw nut mechanism driven by a motor, direct driving of a linear motor, or by pulling of a wire rope driven by a motor.

Figure 8:
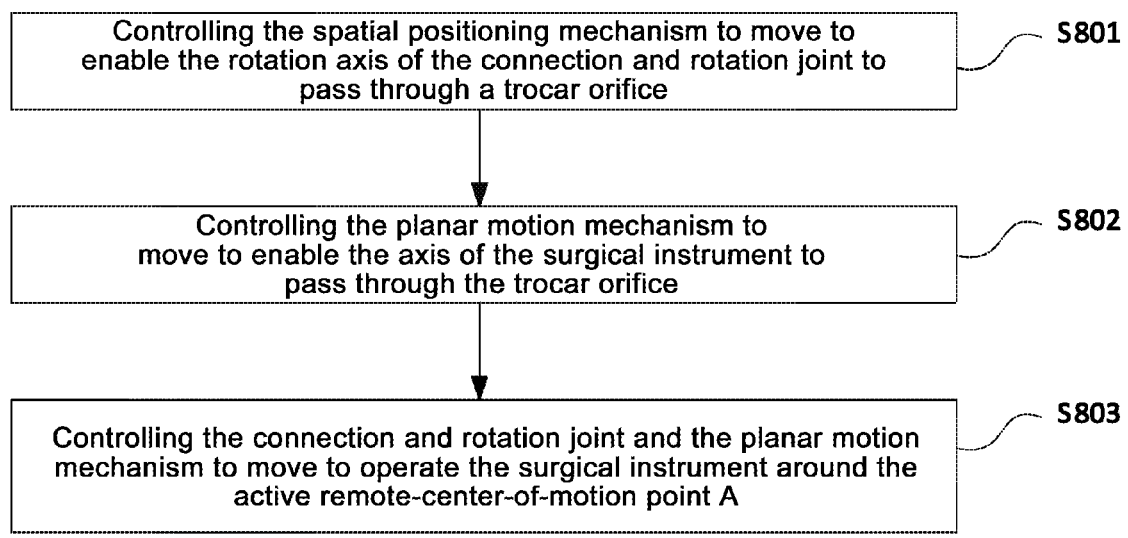
FIG. 8 is a flowchart of a control method for a robotic arm according to the present invention.

In addition, as shown in FIG. 8 and FIG. 5, the present invention further provides a control method for the robotic arm 10 according to any one of the foregoing technical solutions, which includes the following steps.

Step S801. Controlling a spatial positioning mechanism 100 to move to enable the rotation axis of the connection and rotation joint 300 to pass through a trocar orifice. In specific setting, a zero-force control is applied to the joint mechanism of the spatial positioning mechanism 100 to drive the joint mechanism of the spatial positioning mechanism 100, the connection and rotation joint 300, the planar motion mechanism 200, and the surgical instrument 20 to move, thereby ensuring that the rotation axis of the connection and rotation joint 300 passes through the trocar orifice.

Step S802. Controlling the planar motion mechanism 200 to move to enable an axis of the surgical instrument 20 to pass through the trocar orifice. In specific setting, the spatial positioning mechanism 100 is remained stationary to perform a zero-force control on the planar motion mechanism 200. The planar motion mechanism 200 moves to drive the surgical instrument 20 to move accordingly. When the surgical instrument 20 is moved such that the axis of the surgical instrument 20 passes through the trocar orifice, the position of the active remote-center-of-motion point A is adjusted precisely to coincide with the wound.

Step S803. Controlling the connection and rotation joint 300 and the planar motion mechanism 200 to rotate, to rotate the surgical instrument 20 around the active remote-center-of-motion point A. In this case, the active remote-center-of-motion point A is constrained to an optimal position, to meet the foregoing constraint relationship for action control of the active remote-center-of-motion point A.

In the foregoing control method for the robotic arm 10, first, with the step S801, the joints of the joint mechanism of the spatial positioning mechanism 100 are controlled to move relative to the base 110, to drive the connection and rotation joint 300, the planar motion mechanism 200, and the surgical instrument 20 to rotate accordingly, such that the connection and rotation joint 300, the planar motion mechanism 200, and the surgical instrument 20 move in a wide range within a space. In this way, the active remote-center-of-motion point A is positioned in the wide range within the space, such that the rotation axis of the connection and rotation joint 300 passes through the trocar orifice. Then, with the step S802, the planar motion mechanism 200 is controlled to move. The planar motion mechanism 200 moves in the plane perpendicular to the direction of the rotation axis of the connection and rotation joint 300 to drive the surgical instrument 20 to move accordingly, such that the active remote-center-of-motion point A moves in the plane where the planar motion mechanism 200 is located. In this way, the active remote-center-of-motion point A is positioned precisely in the plane where the planar motion mechanism 200 is located, such that the axis of the surgical instrument 20 passes through the trocar orifice, and the active remote-center-of-motion point A is positioned to coincide with the wound. Finally, through the step S803, the connection and rotation joint 300 is controlled to rotate. The connection and rotation joint 300 rotates around its rotation axis, driving the planar motion mechanism 200 and the surgical instrument 20 to rotate accordingly, such that when it is ensured that the active remote-center-of-motion point A remains stationary, the surgical instrument 20 performs a single-degree-of-freedom rotation around the active remote-center-of-motion point A by taking the rotation axis of the connection and rotation joint 300 as a rotation axis. The planar motion mechanism 200 is controlled to rotate to drive the surgical instrument 20 to rotate accordingly, such that when it is ensured that the active remote-center-of-motion point A remains stationary, the surgical instrument 20 performs a single-degree-of-freedom rotation around the active remote-center-of-motion point A by taking the direction perpendicular to the rotation axis of the connection and rotation joint 300 as the rotation axis. According to the foregoing control method for the robotic arm 10, a fixed point can be positioned conveniently and accurately. Moreover, it is ensured that the rotation of the surgical instrument 20 around the active remote-center-of-motion point A can be implemented without requiring the spatial positioning mechanism 100 to move, thereby reducing collision risk which may occur when a plurality of arms move cooperatively.

As shown in FIG. 1, in a preferred implementation, when the tail end of the planar motion mechanism 200 of the robotic arm 10 is connected to the surgical instrument 20 via the first planar moving joint 230, after the connection and rotation joint 300 and the planar motion mechanism 200 are controlled to move, the method further includes:

controlling the first moving joint 230 to move, to operate the surgical instrument through the active remote-center-of-motion point A.

In the foregoing control method for the robotic arm 10, after the step S803, the position of the surgical instrument 20 in the direction perpendicular to the axis of the connection and rotation joint 300 is adjusted by controlling the movement of the first planar moving joint 230, to facilitate the surgical operations.

Various technical features of the foregoing embodiments can be combined in any manner. For simplicity of description, not all possible combinations of the technical features of the foregoing embodiments are described. However, it should be considered to fall within the scope recited in this specification, provided that there is no contradiction between the combinations of these technical features.

The foregoing embodiments are merely representatives of specific implementations of the present application, the descriptions of which are relatively specific and detailed, but should not be construed as limitations to scope of the present application. It should be pointed out that for persons of ordinary skills in the art, several deformations and improvements can be further made without departing from the concept of the present application, and the deformations and improvements all fall within the protection scope of the present application. Therefore, the protection scope of the present application shall be based on the appended claims.

What is claimed is:

1. A robotic arm, comprising
a spatial positioning mechanism, a planar motion mechanism, and a connection and rotation joint connecting the spatial positioning mechanism and the planar motion mechanism, wherein
the spatial positioning mechanism comprises a base and a joint mechanism, the joint mechanism comprising a plurality of joints that are mounted sequentially, wherein one joint of the plurality of joints that is located at a head end of the joint mechanism is mounted onto the base, and one joint of the plurality of joints that is located at a tail end of the joint mechanism is connected to the connection and rotation joint;
the planar motion mechanism comprises a first planar link, a second planar link, a third planar link, a fourth planar link, a first planar rotating joint connected between the first planar link and the second planar link, a second planar rotating joint connected between the second planar link and third second planar link, and a third planar rotating joint connected between the third planar link and the fourth planar link, wherein the first planar link is connected to the connection and rotation joint, the fourth planar link is connected to a surgical instrument; rotation axes of the first planar rotating joint, the second planar rotating joint and the third planar rotating joint are parallel to each other, and are all perpendicular to a rotation axis of the connection and rotation joint; and a perpendicular line of a plane where the planar motion mechanism is located is perpendicular to the rotation axis of the connection and rotation joint; and a point at which the rotation axis of the connection and rotation joint intersects with an axis of the surgical instrument is an active remote-center-of-motion point, and wherein movement of the planar motion mechanism in the plane where the planar motion mechanism is located can make the active remote-center-of-motion point to move along the rotation axis of the connection and rotation joint in the plane where the planar motion mechanism is located, and each of the spatial positioning mechanism, the planar motion mechanism and the connection and rotation joint can be independently controlled to move, and each of the first planar rotating joint, the second planar rotating joint and the third planar rotating joint of the planar motion mechanism can be independently controlled to rotate.

2. The robotic arm according to claim 1, wherein the joint mechanism comprises at least two rotating joints, and a rotation axis of at least one of the rotating joints is perpendicular to the rotation axis of the connection and rotation joint.

3. The robotic arm according to claim 2, wherein the joint mechanism comprises two rotating joints and one moving joint, wherein the moving joint is disposed between the two rotating joints or between the rotating joints and the base, a movement direction of the moving joint is parallel to a rotation axis of one of the rotating joints, and rotation axes of the two rotating joints are perpendicular to each other.

4. The robotic arm according to claim 3, wherein the spatial positioning mechanism further comprises three links, wherein adjacent two of the base and the three links are connected to each other through the moving joint or the rotating joints, and one link of the three links that is farthest to the base is connected to the planar motion mechanism through the connection and rotation joint.

5. The robotic arm according to claim 2, wherein the joint mechanism comprises three rotating joints that are mounted sequentially, wherein one rotating joint of the three rotating joints that is farthest to the connection and rotation joint is mounted onto the base, rotation axes of two rotating joints of the three rotating joints that are close to the base are perpendicular to each other, and rotation axes of two rotating joint of the three rotating joints that are away from the base are parallel to each other.

6. The robotic arm according to claim 5, wherein the spatial positioning mechanism further comprises three links, wherein adjacent two of the base and the three links are connected to each other through the rotating joints, and one link of the three links that is farthest to the base is connected to the planar motion mechanism through the connection and rotation joint.

7. The robotic arm according to claim 2, wherein the joint mechanism comprises two rotating joints and two moving joints, wherein the two moving joints are disposed to be adjacent to each other; movement directions of the two moving joints are perpendicular to each other; one of the rotating joints is disposed between one side of the two moving joints and the base, and the other rotating joint is disposed at another side of the two moving joints; rotation axes of the two rotating joints are perpendicular to each other; and a rotation axis of one rotating joint of the two rotating joints that is disposed adjacent to the base is parallel to a movement direction of one moving joint of the two moving joints that is disposed away from the base.

8. The robotic arm according to claim 7, wherein the spatial positioning mechanism further comprises four links, wherein adjacent two of the base and the four links are connected to each other through the moving joints or the rotating joints, and one link of the four links that is farthest to the base is connected to the planar motion mechanism through the connection and rotation joint.

9. The robotic arm according to claim 1, wherein action control of the active remote-center-of-motion point meets the following constraint relationships:

$$\gamma = \arccos\left(\frac{b^2 + c^2 + e^2}{2bc}\right);$$

$$\beta = \arccos\left(\frac{a^2 + e^2 - d^2}{2ae}\right) + \arccos\left(\frac{b^2 + e^2 - c^2}{2be}\right); \text{ and}$$

$$e = \sqrt{a^2 + d^2 - 2ad * \cos\alpha};$$

wherein, a represents a straight-line distance between center points of rotation of the first planar rotating joint and the second planar rotating joint, b represents a straight-line distance between center points of rotation of the second planar rotating joint and the third planar rotating joint, c represents a straight-line distance between the center point of rotation of the third planar rotating joint and the active remote-center-of-motion point, and d represents a straight-line distance between the center point of rotation of the first planar rotating joint and the active remote-center-of-motion point; and α represents an angle complementary to an angle formed by the first planar link and the second planar link, β represents an angle formed by the second planar link and the third planar link, and γ represents an angle formed by the third planar link and the fourth planar link.

10. The robotic arm according to claim 1, further comprising
a laser generation module disposed on the planar motion mechanism, wherein the laser generation module is coaxially disposed with the connection and rotation joint, and the laser generation module is configured to generate a laser, to illuminate a positioning mark on the surgical instrument so as to indicate the active remote-center-of-motion point.

11. The robotic arm according to claim 10, wherein the positioning mark is coated on a rod surface of the surgical instrument, and a positioning mark area that is illuminated by the laser is a position of the active remote-center-of-motion point.

12. A control method for the robotic arm according to claim 1, comprising:
controlling the spatial positioning mechanism to move to enable the rotation axis of the connection and rotation joint to pass through a trocar orifice;

controlling the planar motion mechanism to move to enable the axis of the surgical instrument to pass through the trocar orifice; and controlling the connection and rotation joint and the planar motion mechanism to move to operate the surgical instrument around the active remote-center-of-motion point.

13. The control method for the robotic arm according to claim 12, wherein when the fourth planar link of the planar motion mechanism of the robotic arm is connected to the surgical instrument through a first planar moving joint, after controlling movements of the connection and rotation joint and the planar motion mechanism, the method further comprises: controlling the first planar moving joint to move to operate the surgical instrument through the active remote-center-of-motion point.

\* \* \* \* \*